(12) United States Patent
Buschmann et al.

(10) Patent No.: US 7,183,274 B2
(45) Date of Patent: Feb. 27, 2007

(54) PIPERIDINE-2,6-DIONES HETEROCYCLICALLY SUBSTITUTED IN THE 3-POSITION

(75) Inventors: Helmut Heinrich Buschmann, Esplugues de Llobregat (ES); Stefanie Frosch, Aachen (DE); Tieno Germann, Aachen (DE); Oswald Karl Zimmer, Wuerselen (DE); Fritz Theil, Berlin (DE)

(73) Assignee: Gruenenthal GmbH, Aachen (DE)

( * ) Notice: Subject to any disclaimer, the term of this patent is extended or adjusted under 35 U.S.C. 154(b) by 231 days.

(21) Appl. No.: 10/871,522

(22) Filed: Jun. 21, 2004

(65) Prior Publication Data

US 2005/0020581 A1    Jan. 27, 2005

Related U.S. Application Data

(63) Continuation of application No. PCT/EP02/14447, filed on Dec. 18, 2002.

(30) Foreign Application Priority Data

Dec. 21, 2001  (DE)  ................ 101 63 595

(51) Int. Cl.
*A61K 31/551* (2006.01)
*A61K 31/517* (2006.01)
*C07D 401/04* (2006.01)
*C07D 401/02* (2006.01)
*C07D 403/02* (2006.01)

(52) U.S. Cl. .................. 514/221; 514/234; 514/321; 514/266.22; 514/316; 540/567; 540/597; 544/126; 544/284; 546/187; 546/199

(58) Field of Classification Search .......... 514/221, 514/234, 321, 266.22, 316; 540/567, 597; 544/126, 284; 546/187, 199
See application file for complete search history.

(56) References Cited

U.S. PATENT DOCUMENTS

| | | | | |
|---|---|---|---|---|
| 5,618,812 A * | 4/1997 | Castro Pineiro et al. | .... | 514/221 |
| 5,665,719 A * | 9/1997 | Bock et al. | .............. | 514/227.8 |
| 6,080,742 A | 6/2000 | Germann et al. | ........ | 514/235.5 |
| 6,656,973 B2 | 12/2003 | Cosenza | ..................... | 514/710 |
| 2004/0048859 A1* | 3/2004 | Germann et al. | ........ | 514/235.5 |
| 2004/0132716 A1* | 7/2004 | Rudolf et al. | .......... | 514/211.15 |

FOREIGN PATENT DOCUMENTS

| | | |
|---|---|---|
| DE | 199 57 342 | 5/2001 |
| DE | 100 02 509 A1 | 7/2001 |
| WO | WO 00/72836 | 12/2000 |

OTHER PUBLICATIONS

An article by Giorgio Ttrinchieri entitled, "Interleukin-12: A Proinflammatory Cytokine with Immunoregulatory Functions that Bridge Innate Resistance and Antigen-Specific Adaptive Immunity," Annual Review of Immunology 1995 13:251-76.
An article by Sylvie Trembleau et al entitled, "The Role of IL-12 in the Induction of Organic-Specific Autoimmune Diseases," Immunology Today, vol. 16, No. 8 1995.
An article by Gabriele Mueller entitled, "IL-12 as Mediator and Adjuvant for the Induction of Contact Sensitivity in Vivo," The Journal of Immunology, pp. 4661-4668, 1995.
An article by Markus F. Neurath et al, "Antibodies of the Interleukin 12 Abrogate Established Experimental Colitis in Mice," The Journal of Experimental Medicine, vol. 182, Nov. 1995, pp. 1281-1290.
An article by Benjamin M. Segal et al entitled, "An Interleukin (IL)-10/IL-12 Immunoregulatory Circuit Controls Susceptibility to Autoimmune Disease," The Journal of Experimental Medicine, vol. 187, No. 4, Feb. 16, 1998, pp. 537-546.
An article by Fiona Powrie entitled, "T Cells in Inflammatory Bowel Disease: Protective and Pathogenic Roles," Immunity, vol. 3 pp. 171-174, Aug. 1995.
An article by Angelika Rudolphi et al entitled, "Polyclonal Expansion of Adoptively Transferred CD4+ αβ T cells in the Colonic Lamina Propria of Scid Mice with Colitis," Eur. J. Immunol. 1996 26:1156-1163.
An article by Alexander H. Enk et al entitled, "Induction of Hapten-specific Tolerance by Interleukin 10 In Vivo," J. Exp. Med. The Rockefeller University Press, 0022-1007/94/04/1397/06, vol. 179 Apr. 1994 pp. 1397-1402.
An article by David F. Fiorentino et al entitled, "IL-10 Acts on the Antigen-Presenting Cell to Inhibit Cytokine Production by Th1 Cells," The Journal of Immunology, vol. 146 3444-3451, No. 10, May 15, 1991.
An article by Rene de Wall Malefyt et al entitled, "Interleukin 10(IL-10) Inhibits Cytokine Synthesis by Human Monocytes: An Autoregulatory Role of IL-10 Produced by Monocytes," J. Exp. Med. The Rockefeller University Press, 0022-1007/91/11/1209/12, vol. 174, Nov. 1991, pp. 1209-1220.
An article by Herve Groux et al entitled, "A CD4+ T-cell Subset Inhibits Antigen-Specific T-cell Responses and Prevents Colitis," Nature, vol. 389 Oct. 16, 1997, pp. 737-742.

(Continued)

*Primary Examiner*—James O. Wilson
*Assistant Examiner*—Tamthom N. Truong
(74) *Attorney, Agent, or Firm*—Crowell & Moring LLP

(57) ABSTRACT

Piperidine-2,6-diones heterocyclically substituted in the 3-position corresponding to formula I

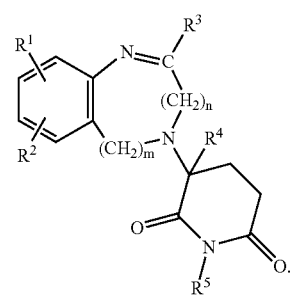

Also the production and use of such compounds in pharmaceutical formulations and related methods of treatment.

33 Claims, No Drawings

OTHER PUBLICATIONS

An article by Soren Bregenholt et al entitled, "Increased Intracellular Th1 Cytokines in Scid Mice with Inflammatory Bowel Disease," Eur. J. Immunol. 1998.28:379-389.

An article by Mario Clerici et al entitled, "Type 1/type 2 Cytokine Modulation of T-cell Programmed Cell Death as a Model for Human Immunodeficiency Virus Pathogenesis," Proc. Natl. Acad. Sci., vol. 91, pp. 11811-11815, Dec. 1994.

An article by Jerome Estaquier et al entitled "T Helper Type 1/T Helper Type 2 Cytokines and T Cell Death: Preventative Effect of Interleukin 12 on Activation-Induced and CD95 (FAS/APO-1)-Mediated Apoptosis of CD4+T Cells from human Immunodeficiency Virus-Infected Persons," J. Exp. Med. The Rockefeller University Press 0022-1007/95/12/1759/09, vol. 182 Dec. 1995 pp. 1759-1767.

An article by Elizabeth P. Sampaio et al entitled, "The Influence of Thalidomide on the Clinical and Immunologic Manifestation of Erythema Nodosum Leprosum," The Journal of Infectious Diseases 1993: 168:408-14.

An article by Jeffrey M. Jacobson entitled, "Thalidomide for the Treatment of Oral Aphthous Ulcers in Patients with Human Immunodeficiency Virus Infection," The New England Journal of Medicine, vol. 336, No. 21, pp. 1487-1493, 1997.

An article by Georgia Vogelsano et al entitled, "Thalidomide for the Treatment of Chronic Graft-Versus-Host Disease," The New England Journal of Medicine, vol. 326, No. 16, pp. 1055-1058, 1992.

An article by Eli D. Ehrenpreis et al entitled, "Thalidomide Therapy for Patients With Refractory Crohn's Disease: An Open-Label Trial," Gastroenterology, 1989; 117: 1271-1277.

An article by Eric Vasiliauskas et al entitled, "Open-Label Pilot Study of Low-Dose Thalidomide in Chronically Active, Steroid-Dependent Crohn's Disease," Gastroenterology, 1999:117:1278-1287.

An article by Bernal et al entitled, "Cellular Immune Effects of Thalidomide in Actinic Prurigo,", 1992, Int. J. Derm 31; 599.

An article by S. Rajkumar et al entitled, "Current Status of Thalidomide in the Treatment of Cancer," Jul. 2001, Oncology, pp. 867-874.

An article by S. Singhal et al entitled, "Antitumor Activity of Thalidomide in Refractory Multiple Myeloma," The New England Journal of Medicine, vol. 341, No. 21, pp. 1565-1609, 1999.

* cited by examiner

PIPERIDINE-2,6-DIONES HETEROCYCLICALLY SUBSTITUTED IN THE 3-POSITION

CROSS-REFERENCE TO RELATED APPLICATIONS

This application is a continuation of International Patent Application No. PCT/EP02/14447, filed Dec. 18, 2002, designating the United States of America, and published in German as WO 03/053956 A1, the entire disclosure of which is incorporated herein by reference. Priority is claimed based on Federal Republic of Germany Patent Application No. DE 101 63 595.8, filed Dec. 21, 2001.

FIELD OF THE INVENTION

The present invention relates to piperidine-2,6-diones heterocyclically substituted in the 3-position of the general formula I

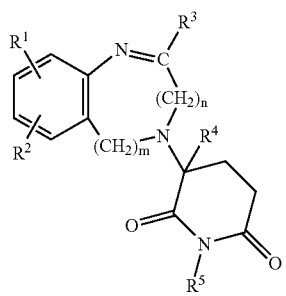

their production, as well as their use in medicaments and related methods of treatment.

BACKGROUND OF THE INVENTION

Autoimmune diseases arise on account of a reactivity of the immune system to the body's own structures. In this connection the tolerance that normally exists with respect to the body's own tissues is destroyed. Apart from antibodies, in particular T lymphocytes and monocytes/macrophages play a decisive role in the pathogenesis of the various autoimmune diseases. Activated monocytes/macrophages secrete a large number of different inflammation-promoting mediators that are directly or indirectly responsible for the destruction of the tissues affected by the autoimmune disease. The activation of monocytes/macrophages takes place either in the interaction with T lymphocytes or via bacterial products such as lipopolysaccharide (LPS). An inflammation-promoting substance formed by activated monocytes/macrophages is interleukin-12 (IL-12).

IL-12 is a heterodimeric molecule that consists of a covalently bound p35 and p40 chain. It is formed by antigen-presenting cells (monocytes/macrophages, dentritic cells, B lymphocytes) after activation by various microbial products such as LPS, lipopeptides, bacterial DNA or in the interaction with activated T lymphocytes (Trinchieri 1995, Ann. Rev. Immunol. 13: 251). IL-12 has a central immuno-regulatory importance and is responsible for the development of inflammation-promoting TH1 reactions. The existence of a TH1 immune reaction to the body's own antigens leads to serious diseases, as is clearly documented in numerous animal experiment and initial clinical investigations. The pathophysiological importance of IL-12 (Trembleau et al. 1995, Immunol. Today 16: 383; Müller et al. 1995 J. Immunol. 155: 4661 Neurath et al. 1995, J. Exp. Med. 182: 1281; Segal et al. 1998. J. Exp. Med. 187: 537; Powrie et al. 1995. Immunity 3: 171; Rudolphi et al. 1996, Eur. J. Immunol. 26: 1156; Bregenholt et al. 1998, Eur. J. Immunol. 28: 379) is manifested in various animal models for diseases such as rheumatoid arthritis, multiple sclerosis, diabetes mellitus as well as inflammatory intestinal, skin and mucous membrane diseases. The respective disease could be triggered by application of IL-12; after neutralisation of endogenous IL-12 there was a remission of the disease symptoms, and eventually a healing of the animals. The use of antibodies against IL-12 in humans is currently being investigated.

The cytokine IL-10 inhibits the synthesis of the inflammation-promoting cytokines TNFα, IL-1, IL-6, IL-8, IL-12 and GM-CSF by human and murine monocytes/macrophages (Fiorentino et al., 1991, J. Immunol. 146: 3444; De Waal Malefyt et al. 1991. J. Exp. Med. 174: 1209). This inhibition also leads indirectly to a blocking of the synthesis of IFN-γ by TH1 lymphocytes. Interestingly, the formation of IL-10 by monocytes/macrophages occurs with a slight time delay compared to the synthesis of the inflammation-promoting cytokines. The treatment of antigen-presenting cells with IL-10 results in their deactivation. Such cells are not able to activate T lymphocytes for the proliferation or the synthesis of IFN-γ. However, these T lymphocytes themselves secrete large amounts of IL-10 and are able to suppress inflammation reactions, as has been shown by the example of an animal model of inflammatory intestinal diseases (Groux et al., 1997. Nature 389: 737). Also, the development of inflammatory skin diseases can be prevented by IL-10 (Enk et al., 1994. J. Exp. Med, 179: 1397).

To summarize, it can be said that an excess of IL-12 or a lack of IL-10 is responsible for the pathophysiology of a large number of inflammatory/autoimmune diseases. Attempts to restore the equilibrium between inflammation-promoting (IL-12) and inflammation-inhibiting (IL-10) cytokines therefore have a large therapeutic potential as regards the diseases mentioned above.

IL-12 is furthermore also involved in the regulation of cell survival. Uncontrolled cell growth is regulated inter alia by apoptosis (programmed cell death). It was shown in T lymphocytes that IL-12 has an anti-apoptotic action and promotes the survival of T cells (Clerici et al. 1994, Proc. Natl. Acad. Sci. USA 91: 11811; Estaquier et al. 1995, J. Exp. Med. 182: 1759). A localized over-production of IL-12 may therefore contribute to the survival of tumor cells. Inhibitors of the formation of IL-12 accordingly also have a large therapeutic potential in the treatment of tumors.

A substance having the immunomodulating effect of inhibiting IL-12 and increasing IL-10 is thalidomide. Recent clinical studies have shown the positive influence of thalidomide on the following diseases: erythema nodosum leprosum (Sampaio et al. 1993, J. Infect. Dis. 168: 408), aphthosis (Jacobson et al. 1997, N. Engl. J. Med. 336: 1487), chronic rejection reactions (Vogelsang, et al. 1992, N. Engl. J. Med. 326: 1055), inflammatory intestinal diseases (Ehrenpreis et al. 1999, Gastroenterology 117: 1271); Vasitiauskas et al. 1999, Gastroenterology 117: 1278) as well as numerous skin diseases {Bernal et al. 1992, Int. J. Derm. 31; 599). Clinical studies are also in progress on the treatment of a number of tumor diseases (Rajkumar, 2001, Oncology 15: 867). An effect on multiple myeloma appears certain (Singhal, 1999, N. Engl. J. Med. 341: 1565). However, thalidomide also gives rise to a number of side effects, including sedation, teratogenicity and neuropathy. In addition the substance is sparingly soluble and highly sensitive to hydrolysis.

SUMMARY OF THE INVENTION

One object of the invention is to provide novel compounds that exhibit the immunomodulating principle described above and that furthermore are less sensitive to hydrolysis and have improved solubility.

Certain substituted piperidine-2,6-diones are included within the invention.

The invention accordingly provides piperidine-2,6-diones heterocyclically substituted in the 3-position of the general formula I

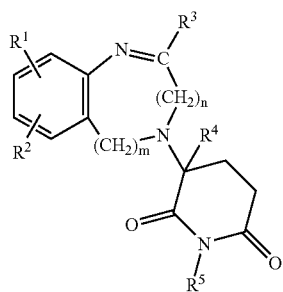

in which

R$^1$ and R$^2$ which are identical or different, denote H, Br, Cl, F, CF$_3$, OH, NO$_2$, NH$_2$, N(CH$_3$)$_2$, C$_{1-3}$-alkyl, C$_{1-3}$-alkoxy, phenyl, or together form an annelated benzene ring, in which the rings are optionally substituted by R$^1$ and/or R$^2$ and R$^1$ and R$^2$ are as defined above, R$^3$ denotes H, the methyl group or, in the case where a C—N single bond is present, denotes OH, C$_{1-3}$-alkoxy or an [O(CO)C$_{1-3}$-alkyl] group, or together with the C atom forms a carbonyl group, R$^4$ denotes H, F, CF$_3$ or C$_{1-3}$-alky, R$^5$ denotes H, a CH$_2$—OH group or a CH$_2$—NR$^6$R$^7$ radical, in which R$^6$ and R$^7$ are identical or different and denote an alkyl group with 1 to 6 C atoms (straight-chain or branched) or together with the N atom denote a pyrrolidine, piperidine, hexamethyleneimine or morpholine ring, n is 0 or 1 and m is 0, 1 or 2.

The compounds according to the invention may exist as pure enantiomers or non-racemic enantiomer mixtures, racemates, diastereomers or diastereomer mixtures, in the form of their free bases as well as in the form of salts with physiologically compatible organic or inorganic acids.

Preferred compounds are those in which R$^1$ and R$^2$, identical or different from one another, denote H, Br, Cl, F, CF$_3$, NO$_2$, NH$_2$, C$_{1-3}$-alkyl, C$_{1-3}$-alkoxy, or together form an annelated benzene ring, R$^3$ denotes H or OH, R$^4$ denotes H or a methyl group and R$^5$ denotes H or a CH$_2$—NR$^6$R$^7$ radical, in which R$^6$ and R$^7$ together with the N atom form a piperidine ring, and n=0 and m=1 or 2.

Particularly preferred are compounds in which R$^1$ and R$^2$, identical or different from one another, denote H, Cl, F, CH$_3$ or NO$_2$, R$^3$, R$^4$ and R$^5$ denote hydrogen, n=0 and m=1, and a C=N double bond is present.

Further preferred compounds include:

3-(7-chloro-4H-quinazolin-3-yl)piperidine-2,6-dione and the corresponding hydrobromide;
3-(6-chloro-4H-quinazolin-3-yl)piperidine-2,6-dione and the corresponding hydrobromide;
3-(4H-quinazolin-3-yl)piperidine-2,6-dione and the corresponding hydrobromide or hydrochloride;
3-(2-hydroxy-1,4-dihydro-2H-quinazolin-3-yl)piperidine-2,6-dione;
3-(6-methoxy-4H-quinazolin-3-yl)piperidine-2,6-dione and the corresponding hydrochloride;
3-(5-chloro-4H-quinazolin-3-yl)piperidine-2,6-dione;
3-(8-chloro-4H-quinazolin-3-yl)piperidine-2,6-dione;
3-(6-fluoro-4H-quinazolin-3-yl)piperidine-2,6-dione;
3-(8-methoxy-4H-quinazolin-3-yl)piperidine-2,6-dione and the corresponding hydrochloride;
3-(7-fluoro-4H-quinazolin-3-yl)piperidine-2,6-dione and the corresponding hydrochloride;
3-(4H-benzo[g]quinazolin-3-yl)piperidine-2,6-dione;
3-(5-fluoro-4H-quinazolin-3-yl)piperidine-2,6-dione;
3-(5-nitro-4H-quinazolin-3-yl)piperidine-2,6-dione;
3-(7-trifluoromethyl)-4H-quinazolin-3-yl)piperidine-2,6-dione;
3-(7-nitro-4H-quinazolin-3-yl)piperidine-2,6-dione;
3-(8-bromo-6-methyl-4H-quinazolin-3-yl)piperidine-2,6-dione;
3-(5-methyl-4H-quinazolin-3-yl)piperidine-2,6-dione;
3-(6,7-difluoro-4H-quinazolin-3-y])piperidine-2,6-dione;
3-methyl-3-(4H-quinazolin-3-yl)piperidine-2,6-dione;
3-(4,5-dihydrobenzo[d][1,3]diazepin-3-yl)piperidine-2,6-dione;
3-(5-amino-4H-quinazolin-3-yl)piperidine-2,6-dione and the corresponding dihydrochloride;
3-(7-amino-4H-quinazolin-3-yl)piperidine-2,6-dione and the corresponding dihydrochloride and
3-(7-fluoro-4H-quinazolin-3-yl)1-piperidin-1-ylmethyl-piperidine-2,6-dione.

Particularly preferred compounds include:

3-(7-chloro-4H-quinazolin-3-yl)piperidine-2,6-dione and the corresponding hydrobromide;
3-(4H-quinazolin-3-yl)piperidine-2,6-dione and the corresponding hydrobromide;
3-(5-chloro-4H-quinazolin-3-yl)piperidine-2,6-dione;
3-(7-fluoro-4H-quinazolin-3-yl)piperidine-2,6-dione and the corresponding hydrochloride and
3-(5-fluoro-4H-quinazolin-3-yl)piperidine-2,6-dione.

The present invention also provides processes for the production of these compounds according to the invention of the formula I.

The compounds of the formula I are obtained by first of all alkylating an amino compound of the general formula II

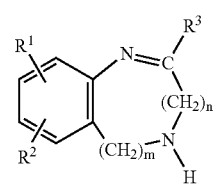

with a 3-bromopiperidine-2,6-dione derivative of the general formula III

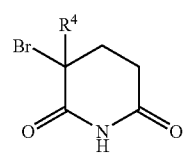

to form a compound of the general formula IA

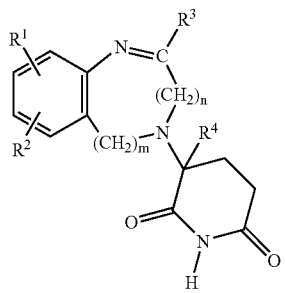

IA wherein in the compounds IA, II and III the radicals $R^1$ to $R^4$ are defined as above, and then, if $R^5$ is not intended to denote hydrogen, introducing this radical by reaction with formaldehyde, optionally together with an amine of the general formula $HNR^6R^7$, in which $R^6$ and $R^7$ are as defined above.

If, in the compound of the formula IA the radical $R^4$ denotes hydrogen, then this can be replaced by means of alkylation or halogenation reactions known per se by the other $R^4$ substituents defined above.

If, in the compound of the formula IA $R^1$ and/or $R^2$ denote a nitro group, then compounds IA in which $R^1$ and/or $R^2$ denote the amino group can be produced in a manner known per se, for example by reduction with catalytically excited hydrogen.

Compounds of the formula I are also obtained by alkylating an amino compound of the formula II first of all with a 3-bromopiperidin-2-one derivative of the formula IV

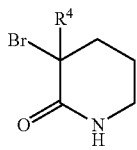

IV to form a compound of the general formula IB

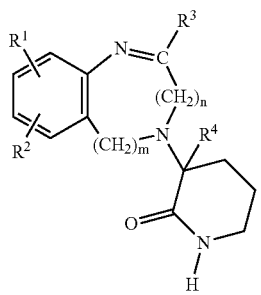

IB and this is oxidized, preferably with m-chloroperbenzoic acid or ruthenium (IV) oxide/sodium periodate to form a compound of the aforementioned formula IA, and optionally other radicals $R^4$ and/or the radical $R^5$ are introduced.

Preferred compounds of the formula I, in which m=1 and n=0 and $R^3$ denotes H or OH, are produced by first of all oxidizing in a manner known per se, for example with pyridinium dichromate, a formamide derivative of the general formula VI

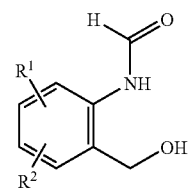

VI in which $R^1$ and $R^2$ are as defined above and which is accessible by selective N-formylation of the corresponding 2-aminobenzyl alcohol or by selected O-deformylation of the N,O-bisformyl derivative, for example enzymatically with the aid of CAL-B, to form a benzaldehyde of the general formula VII

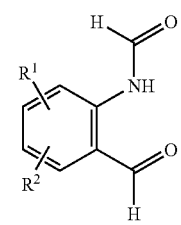

VII which is converted by reductive amination with glutamine using complex boron hydrides, for example sodium borohydride, into compounds of the general formula VIII.

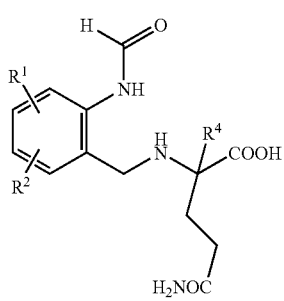

VIII

These compounds of the general formula VIII can then be cyclized, for example with N,N'-carbonyl diimidazole, to form glutarimides of the general formula IX, preferably after prior protection of the amine function by for example the benzoyloxycarbonyl group, which is then split off again, for example with hydrogen bromide in glacial acetic acid.

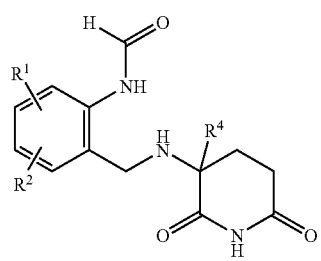

IX

From these compounds of the general formula IX there are finally obtained in protic solvents, for example water under acid catalysis, compounds of the general formula I in which $R^1$, $R^2$ and $R^4$ are as defined above, m=1, n=0, a C=N double bond is present, and $R^3$ and/or $R^5$ denote a hydrogen atom, which in the case of $R^5$ can, as described above, be replaced by the other substituents according to the definition.

If in the compounds of the general formula IX in which the amine function is protected by the benzyloxycarbonyl radical this radical is split off hydrogenolytically, then compounds of the general formula I are obtained in which $R^1$ and $R^2$ are as defined above, a C—N single bond is present, and $R^3$ denotes a hydroxy group. These compounds can be converted by splitting off water by means of dilute acids in organic solvents, for example methanol, into compounds of the general formula I with a C=N double bond and where $R^3$=hydrogen.

If after reductive amination of the compounds of the general formula VII the reaction mixture is treated with acids, then compounds of the general formula X in which $R^1$, $R^2$ and $R^4$ are as defined above are obtained therefrom,

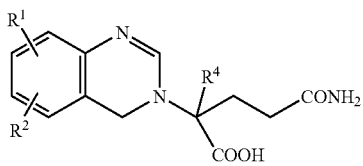

X which can be converted by cyclization, for example with acetic anhydride/acetyl chloride, into compounds of the general formula I in which m=1 and n=0, a C=N double bond is present, $R^1$, $R^2$ and $R^4$ are as defined above, and $R^3$ and/or $R^5$ denote hydrogen. Following this other radicals $R^4$ and/or $R^5$ according to the definitions are optionally introduced as described above.

In a similar way compounds of the formula I can also be obtained in which n=2 and the other radicals are as defined above.

The compounds according to the invention have an immunomodulating activity, and induce a sharp reduction of IL-12 production in LPS-activated monocytes with a simultaneous rise in IL-10 production. On account of this effect principle these compounds have an important therapeutic potential in diseases where an excessive IL-12 production and a relative lack of IL-10 are responsible for the pathogenesis, in other words such compounds can be used for the treatment and/or prophylaxis of inflammatory and autoimmune diseases. On account of the anti-apototic action of IL-12, the compounds according to the invention are also suitable for suppressing the formation of IL-12 in haematological/oncological diseases.

This distinguishes the claimed compounds from known immunomodulators such as corticosteroids (e.g. dexamethasone), which suppress the synthesis of IL-12 as well as that of IL-10 by monocytes.

Compared to thalidomide the new compounds are surprisingly characterized by an improved efficacy, a good solubility in water as well as a reduced sensitivity to hydrolysis.

The diseases of the types mentioned above include inter alia inflammations of the skin (e.g. atopic dermatitis, psoriasis, eczema, erythema nodosum leprosum), inflammations of the respiratory pathways (e.g. bronchitis, pneumonia, bronchial asthma, ARDS (Adult Respiratory Distress Syndrome), sarcoidosis, silicosis/fibrosis), inflammations of the gastrointestinal tract (e.g. gastroduodenal ulcers, Crohn's disease, ulcerative colitis), as well as diseases such as hepatitis, pancreatitis, appendicitis, peritonitis, nephritis, aphtosis, conjunctivitis, keratitis, uveitis and rhinitis. The autoimmune diseases include for example diseases of the arthritis group (e.g. rheumatoid arthritis, HLA-B27 associated diseases, rheumatoid spondylitis), as well as multiple sclerosis, early onset diabetes or lupus erythematosus. Further indications for use include sepsis, septic shock, bacterial meningitis, mycobacterial infections, opportunistic infections with AIDS, cachexia, transplant rejection reactions, graft-versus-host reactions, as well as chronic heart failure, cardiac insufficiency, reperfusion syndrome and also atherosclerosis. Medical indications for use furthermore include chronic pain states, fibromyalgia, and Sudeck's disease (Reflex Sympathetic Dystrophy (RSD)).

Clinical conditions in which the described immunomodulators can be used also include haematological diseases such as multiple myeloma, myelodisplastic syndrome and leukaemias, as well as further oncological conditions for example glioblastoma, prostate cancer, renal cell carcinoma, breast cancer, thyroid, head and neck cancer, pancreatic cancer and colorectal cancer, as well as melanoma and Kaposi's sarcoma.

Medicaments according to the invention contain, in addition to at least one compound of the general formula I, also carrier materials, fillers, solvents, diluents, colorants and/or binders. The choice of the auxiliary substances as well as the amounts thereof to be used depend on whether the medicament is to be applied orally, rectally, ophthalmically (intravitreal, intracameral), nasally, topically (including buccal and sublingual), vaginally or parenterally (including subcutaneous, intramuscular, intravenous, intradermal, intratracheal and epidural).

For oral applications suitable preparations are in the form of tablets, chewable tablets, sugar-coated pills, capsules, granules, drops, juices or syrups, while for parenteral, topical and inhalative application suitable preparations include solutions, suspensions, readily reconstitutable dry preparations, as well as sprays. Cutaneous application forms include ointments, gels, creams and pastes. Ophthalmic application forms include drops, ointments and gels. Compounds according to the invention in depot form in solution, a carrier film or a plaster, optionally with the addition of agents promoting penetration of the skin, are examples of suitable percutaneous application forms. The compounds according to the invention can be released in a delayed manner from orally or percutaneously usable preparation forms.

The amount of active substance to be administered to the patient varies depending on the patient's weight, type of administration, medical indications and the severity of the disease.

EXAMPLES

The following examples serve to illustrate certain embodiments of the present invention in more detail, and they are not intended to, and should not be understood to, limit the claims appended hereto.

Silica gel 60 (0.040 to 0.063 mm) from E. Merck, Darmstadt, was used as stationary phase for the chromatographic separations. The mixture ratios of the eluents are always specified in volume/volume.

The substances were characterized via their melting point and/or the $^1$H-NMR spectrum. The spectra were recorded at 300 MHz with a Varian Gemini 300 instrument. The chemical shifts are given in ppm (δ scale). Tetramethylsilane (TMS) was used as internal standard.

Example 1

3-(7-chloro-4H-quinazolin-3-yl)piperidine-2,6-dione; hydrobromide

Stage 1:
N-(5-chloro-2-hydoxymethylphenyl)formamide

A solution of 5.00 g of (2-amino-4-chlorophenyl)methanol, 2.73 g of cyanomethyl formate and 0.04 g of 4-N,N-dimethylaminopyridine in 50 ml of anhydrous tetrahydrofuran was stirred for 72 hours at 20° C. The solvent was then evaporated in vacuo and the residue was taken up in 50 ml of ethyl acetate. The solution was washed in succession twice with in each case 100 ml of 0.01 N hydrochloric acid and saturated sodium chloride solution, dried over sodium sulfate and then concentrated by evaporation in vacuo. The residue was purified by flash chromatography on silica gel with ethyl acetate/cyclohexane (2/1) as eluent. 1.41 g (24% of theory) of the title compound was thereby obtained in the form of slightly yellowish crystals.

Melting point: 120–124° C.

Stage 2:
N-(5-chloro-2-formylphenyl)formamide

A mixture of 1.40 g of the product from stage 1 and 3.40 g of pyridinium dichromate in 350 ml of anhydrous dichloromethane was stirred for 24 hours at 20° C. The solution was then filtered and the filtrate was concentrated by evaporation in vacuo. The residue was purified by flash chromatography on silica gel with ethyl acetate/cyclohexane (1/1) as eluent, 0.88 g (64% of theory) of the title compound being obtained in crystalline form.

Melting point: 131–136° C.

Stage 3:
2-[benzyloxycarbonyl-4-chloro-2-formylaminobenzyl)amino]-4-carbamoylbutyric acid A solution of 1.02 g of the product from stage 2 in 12 ml of tetrahydrofuran was added to a solution of 0.75 g of L-glutamine in 2.8 ml of 2 N sodium hydroxide solution. The mixture was stirred for 1 hour at 20° C., cooled to 0° C., and 0.13 g of sodium borohydride was added in portions. After 12 hours' stirring at 20° C., a solution of 1.47 g of pyrocarbonic acid dibenzyl ester in 5.5 ml of tetrahydrofuran was added dropwise within one hour; 2 ml of 2 N sodium hydroxide solution were then added. After 12 hours' stirring at 20° C., tetrahydrofuran was largely evaporated in vacuo and the residue was extracted three times with 20 ml of diethyl ether each time. The aqueous phase was acidified to pH 1 with 2N hydrochloric acid and extracted three times with 20 ml of ethyl acetate each time. The combined organic phases were dried over sodium sulfate and concentrated by evaporation in vacuo, 0.99 g (40% of theory) of the title compound being obtained, which was reacted further without purification.

Stage 4:
(4-chloro-2-formylaminobenzyl)-(2,6-dioxopiperidin-3-yl)carbamic acid benzyl ester A solution of 0.98 g of the product from stage 3 and 0.97 g of N,N'-carbonyldiimidazole in 50 ml of anhydrous tetrahydrofuran was heated under reflux for 8 hours. After cooling, the mixture was concentrated by evaporation in vacuo, the residue was taken up in 40 ml of water and 40 ml of ethyl acetate, and the organic phase was separated. The aqueous phase was extracted three times with 20 ml of ethyl acetate each time. The combined organic phases were washed three times with 20 ml of water each time, then with 20 ml of saturated sodium chloride solution, dried over sodium sulfate, and concentrated by evaporation in vacuo. After purifying the residue by flash chromatography on silica gel with ethyl acetate/cyclohexane (1/1), 0.37 g (16% of theory, referred to the product of stage 2) of the title compound remained.

Stage 5:
N-{5-chloro-2-[(2,6-dioxopiperidin-3-ylamino)methyl]-phenyl}formamide; hydrobromide 0.9 ml of hydrobromic acid in acetic acid (33% HBr) was added to a solution of 0.38 g of the product from stage 4 in 2 ml of acetic acid and the mixture was stirred for 1 hour at 20° C. 400 ml of diethyl ether were then poured in, the mixture was cooled to 0° C., and the precipitated solid was separated off. This solid was washed several times with diethyl ether and dried in vacuo, 0.27 g (83% of theory) of the title compound being obtained in the form of colorless crystals.

Melting point: 155–180° C. (decomposition)

Stage 6:
3-(7-chloro-4H-quinazolin-3-yl)piperidine-2,6-dione; hydrobromide

A solution of 0.20 g of the product from stage 5 in 10 ml of distilled water was stirred for 72 hours at 20° C. The mixture was then filtered, the filtrate was concentrated by evaporation in vacuo, and the residue was dried. 0.13 g (68% of theory) of the title compound was obtained as a white solid.

Melting point: 160–200° C. (decomposition)

$^1$H-NMR (DMSO-$d_6$): 2.57 (m, 2H); 2.82 (m, 2H); 4.80 (m, 1H); 4.95 (m, 1H); 5.10 (m, 1H) 7.30 (m, 2H); 7.45 (m, 1H); 8.68 (s, 1H); 11.42 (s, 1H)

Example 2

3-(6-chloro-4H-quinazolin-3-yl)piperidine-2,6-dione; hydrobromide

By replacing the benzyl alcohol used in Example 1, stage 1, by the 5-chloro isomer and adopting the procedure described in stages 1 to 6, the title compound was obtained in the form of pale yellow crystals.

$^1$H-NMR (DMSO-$d_6$): 2.19 (m, 1H); 2.43 (m, 1H); 2.75 (m, 2H); 4.78 (m, 2H); 5.02 (m, 1H); 7.18 (d, 1H); 7.38 (d, 1H); 7.45 (q, 1H); 8.59 (s, 1H); 11.35 (s, 1H)

Example 3

3-(4H-quinazolin-3-yl)piperidine-2,6-dione; hydrobromide

Stage 1:
(2-formylaminobenzyl)-(2,6-dioxopiperidin-3-yl) carbamic acid benzyl ester By using (2-aminophenyl)methanol in Example 1, stage 1 and adopting the procedure described in stages 1 to 4, the title compound was obtained in the form of a yellow powder.

Stage 2:
N-{2-[(2,6-dioxopiperidin-3-ylamino)methyl]phenyl}formamide; hydrobromide 1.00 g of the product from stage 1 was reacted as described in Example 1, stage 5, with 3 ml of hydrobromic acid in acetic acid (33% HBr). After similar working-up, 0.79 g (91% of theory) of the title compound was obtained in the form of a yellowish solid, which was reacted further without purification.

Stage 3:

3-(4-H-quinazolin-3-yl)piperidine-2,6-dione; hydrobromide

A solution of 0.91 g of the product from stage 2 in 5 ml of distilled water was stirred for 24 hours at 20° C. The reaction solution was then evaporated to dryness in vacuo. The remaining solid was triturated with diethyl ether, 0.85 g (99% of theory) of the title compound remaining as a yellow powder.

Melting point: 218–222° C. (decomposition)

$^1$H-NMR (DMSO-d$_6$): 2.23 (m, 1H); 2.48 (m, 1H); 2.71 (m, 2H); 4.70 (d, 1H); 4.86 (d, 1H); 4.98 (m, 1H); 7.22 (m, 2H); 7.34 (m, 2H); 8.53 (s, 1H); 11.35 (s, 1H)

Example 4

3-(2-hydroxy-1,4-dihydro-2H-quinazolin-3-yl)piperidine-2,6-dione 15.90 g of the product from Example 3, stage 1, dissolved in 950 ml of tetrahydrofuran were hydrogenated over 15 g of palladium on activated charcoal (10% Pd) at 20° C. under normal pressure. After removing the catalyst by filtration, the filtrate was concentrated by evaporation in vacuo. 10.30 g (98% of theory) of the title compound remained as a diastereomer mixture in the form of a white solid.

Melting point: 185–188° C.

Example 5

3-(4H-quinazolin-3-yl)piperidine-2,6-dione; hydrochloride

A solution of 10.20 g of the product from Example 4 in 210 ml of methanol and 3.2 ml of 12 N hydrochloric acid was stirred for 24 hours at 20° C. The mixture was then largely concentrated by evaporation in vacuo, the title compound being obtained in crystalline form, 9.00 g (82% of theory) of which remained after separation by filtration and drying.

Melting point: 172–178° C.

$^1$H-NMR (DMSO-d$_6$): 2.22 (m, 1H); 2.48 (m, 1H); 2.71 (m, 2H); 4.70 (d, 1H); 4.86 (d, 1H); 4.98 (m, 1H); 7.22 (m, 2H); 7.35 (m, 2H); 8.53 (s, 1H); 11.35 (s, 1H).

Example 6

3-(6-methoxy-4H-quinazolin-3-yl)piperidine-2,6-dione; hydrochloride

Stage 1:

Formic acid (2-formylamino-5-methoxybenzyl)ester

A solution of 7.00 g of (2-amino-5-methoxyphenyl)methanol, 9.8 ml of formic acid cyanomethyl ester and 0.05 g of 4-N,N-(dimethylamino)pyridine in 30 ml of anhydrous tetrahydrofuran was heated for 5 hours under reflux. The solution was then concentrated by evaporation in vacuo and the residue was taken up in 100 ml of ethyl acetate. Crystals formed on cooling the solution to 0° C., which were suction filtered, washed with methanol, and dried in vacuo. 7.20 g (75% of theory) of the title compound were thereby obtained.

Melting point: 117° C.

Stage 2:

N-(2-hydroxymethyl-4-methoxyphenyl)formamide 1.70 g of Candida antarctica B lipase (CAL-B) were added to a solution of 5.90 g of the product from stage 1 in a mixture of 190 ml of anhydrous acetonitrile and 10.3 ml of n-butanol and stirred for 65 hours at 20° C. The mixture was then filtered and washed with acetonitrile. After concentrating the filtrate by evaporation in vacuo, 5.00 g (98% of theory) of the title compound remained.

Melting point 97–98° C.

Stage 3:

N-(2-formyl-4-methoxyphenyl)formamide 5.00 g of the product from stage 2 were oxidised with pyridinium dichromate as described in Example 1, stage 2, 3.62 g (72% of theory) of the title compound being obtained.

Melting point: 125–127° C.

Stage 4:

4-carbamoyl-2-(6-methoxy-4H-quinazolin-3-yl)butanoic acid

A solution of 0.79 g of the product from stage 3 in 30 ml of methanol was added to a solution of 0.58 g of L-glutamine in 10 ml of methanol and 2 ml of 2N sodium hydroxide solution. After stirring for 1 hour at 20° C., the mixture was cooled to 0° C. and 0.103 g of sodium borohydride was added in portions within 30 minutes. The mixture was stirred for 12 hours at 0° C., then adjusted to pH 2 to 3, and stirred for a further 4 hours at 20° C. After neutralizing the solution with sodium hydroxide, the methanol was distilled off. The aqueous residue was washed twice with 15 ml of diethyl ether each time, and then concentrated by evaporation in vacuo. The residue was taken up in 25 ml of methanol and freed from insoluble constituents by filtration. The residue obtained by evaporating the filtrate in vacuo was directly reacted further as described in stage 5, without purification.

Stage 5:

3-(6-methoxy-4H-quinazolin-3-yl)piperidine-2,6-dione; hydrochloride

A solution of 1.20 g of the crude product from stage 4 in 7 ml of acetic anhydride and 7 ml of acetyl chloride was stirred for 5 hours at 70° C. and then concentrated by evaporation in vacuo. The residue was taken up in 20 ml of methanol and stirred for 1 hour with Amberlyst A-21 ion exchanger. After filtration the filtrate was concentrated by evaporation in vacuo and the residue was purified by flash chromatography with chloroform/methanol (4/1) as eluent. The free base of the title compound thereby obtained was dissolved in 4 ml of methanol and 0.5 ml of a saturated solution of HCl gas in diethyl ether followed by 150 ml of diethyl ether were added to the solution. The salt formed was separated and dried in vacuo, 0.29 g (23% of theory referred to L-glutamine in stage 4) of the title compound being obtained.

$^1$H-NMR (DMSO-d$_6$): 2.45 (m, 4H); 3.76 (s, 3H); 4.65 (d, 1H); 4.81 (d, 1H); 4.98 (m, 1H) 6.88 (m, 2H); 7.20 (m, 1H); 8.46 (5, 1H); 11.32 (s, 1H)

Example 7

Using appropriately substituted educts and applying the procedure described in Example 6, the following compounds were similarly obtained (in some cases without conversion to the hydrochloride):

a) 3-(5-chloro-4H-quinazolin-3-yl)piperidine-2.6-dione
   Melting point: 245–250° C. (decomposition)
b) 3-(8-chloro-4H-quinazolin-3-yl)piperidine-2,6-dione
   Melting point: 238–248° C.
c) 3-(6-fluoro-4H-quinazolin-3-yl)piperidine-2.6-dione
   Melting point: 75–79° C.
d) 3-(8-methoxy-4H-quinazolin-3-yl)piperidine-2.6-dione; hydrochloride
   Melting point: 152–159° C.

e) 3-(7-fluoro-4H-quinazolin-3-yl)piperidine-2,6-dione
   Melting point: 239–241° C. (decomposition)
f) 3-(7-fluoro-4H-quinazolin-3-yl)piperidine-2,6-dione; hydrochloride
   Melting point: 205–207° C.
g) 3-(4H-benzo[g]quinazolin-3-yl)piperidine-2.6-dione
   Melting point: 238–242° C.
h) 3-(5-fluoro-4H-quinazolin-3-yl)piperidine-2.6-dione
   Melting point: 237–239° C. (decomposition)
i) 3-(5-nitro-4H-ginazolin-3-yl)piperidine-2,6-dione
   Melting point: 197–215° C.
j) 3-(7-trifluoromethyl)-4H-quinazolin-3-yl)piperidine-2,6-dione
   Melting point: 230–234° C.
k) 3-(7-nitro-4H-quinazolin-3-yl)piperidine-2,6-dione
   Melting point: >360° C.
l) 3-(8-bromo-6-methyl-4H-quinazolin-3-yl)piperidine-2,6-dione
   Melting point: 258–265° C.
m) 3-(5-methyl-4H-quinazolin-3-yl)piperidine-2,6-dione
   Melting point: 217–227° C.
n) 3-(6,7-difluoro-4H-quinazolin-3-yl)piperidine-2,6-dione
   Melting point: from 360° C. (decomposition)
o) 3-methyl-3-(4H-quinazolin-3-yl)piperidin-2,6-dione
   $^1$H-NMR (DMSO-$d_6$): 1.59 (s, 3H); 1.93–2.70 (m, 4H); 4.35 (d, 1H); 4.47 (d, 1H); 6.90–7.15 (m, 4H); 7.36 (s, 1H); 11.04 (s, 1H)

Example 8

3-(4,5-dihydrobenzo[d][1,3]diazepin-3-yl)piperidine-2, 6-dione

Stage 1:
N-[2-(2-hydroxyethyl)phenyl]formamide 12.6 ml of formic acid were added dropwise at 0° C. to 15 ml of acetic anhydride, and the mixture was then stirred for 2 hours at 60° C. After cooling to 20° C., the mixture was diluted with 140 ml of tetrahydrofuran, cooled to −4° C., and at this temperature a solution of 18.4 g of 2-(2-aminophenyl) ethanol in 185 ml of tetrahydrofuran was added dropwise. After stirring for 3 hours at −6° C. the mixture was neutralised with aqueous potassium hydrogen carbonate solution (25% $KHCO_3$) and extracted four times with 300 ml of ethyl acetate each time. The combined extracts were dried over sodium sulfate and concentrated by evaporation in vacuo. 18.4 g (94% of theory) of the title compound were thereby obtained in the form of yellowish crystals that melted at 49–54° C.

Stage 2:
N-[2-(2-oxoethyl)phenyl]formamide or 2-hydroxy-2,3-dihydroindole-1-carbaldehyde 49.4 g of pyridinium dichromate were added at 0° C. under stirring to a solution of 18.2 g of the product from stage 1 in 270 ml of anhydrous dichloroethane and the mixture was then stirred for 24 hours at 40° C. After filtration through celite, the filtrate was concentrated by evaporation in vacuo and the residue was purified by flash chromatography on silica gel with ethyl acetate/cyclohexane (1/1) as eluent. 7.5 g (42% of theory) of the title compound were thereby obtained as a yellowish solid, which melted at 84–91° C. with decomposition.

Stage 3:
4-carbamoyl-2-(4,5-dihydrobenzo[d][1,3]diazepin-3-yl) butyric acid

A solution of 4.6 g of the product from stage 2 in 110 ml of methanol was added to a solution of 4.1 g of L-glutamine in 14 ml of 2N sodium hydroxide solution and 7 ml of methanol and the mixture was stirred for 2 hours at 20° C. The mixture was then cooled to 0° C., 0.64 g of sodium borohydride was added in portions, and the mixture was stirred for a further 12 hours at 0° C. The reaction solution was adjusted to a pH of 3.5 with 2N hydrochloric acid and stirred for 20 hours at 20° C. After neutralisation with sodium hydroxide solution, the solid formed was separated by filtration and the filtrate was freed from methanol in vacuo. From the aqueous residue 3.0 g (39% of theory) of the crude title compound were isolated, which were used without purification for the further reaction.

Stage 4:
3-(4,5-dihydrobenzo[1][1,3]diazepin-3-yl)piperidine-2,6-dione 12 ml of acetyl chloride were added to 3.0 g of the product from stage 3 in 12 ml of acetic anhydride. The mixture was stirred for 32 hours under reflux and for 66 hours at 50° C., and was then concentrated by evaporation in vacuo. The residue was purified by flash chromatography on silica gel with trichloromethane/methanol (4/1) as eluent, 0.79 g (28% of theory) of the title compound being obtained as a yellowish solid, which melted starting at 250° C. with decomposition.

$^1$H-NMR (DMSO-$d_6$/$D_2O$): 2.10–2.20 (m, 1H); 2.25–2.40 (m, 1H); 2.60–2.75 (m, 2H); 3.10–3.14 (m, 2H); 3.54–3.85 (m, 2H) 4.89 (dd, 1H); 7.10–7.30 (m, 4H); 7.77 (s, 1H)

Example 9 a) 3-(5-amino-4H-quinazolin-3-yl)piperidine-2,6-dione; dihydrochloride

A solution of 0.315 g of the product from Example 7i in 11 ml of N,N-dimethylformamide and 1.1 ml of 2N hydrochloric acid was catalytically hydrogenated over 0.057 g of platinum dioxide (80%) at 20° C. under a hydrogen pressure of 3 bar. The catalyst was then separated by filtration and the filtrate was concentrated by evaporation in vacuo. The remaining solid was treated several times with toluene and diethyl ether and dried over phosphorus pentoxide. 0.32 g (88% of theory) of the title compound was thereby obtained in the form of dark-colored crystals, which underwent deliquescence in air.

$^1$H-NMR (DMSO-$d_6$): 2.10–2.80 (m, 4H); 4.35 (d, 1H); 4.56 (d, 1H); 5.03 (dd, 1H); 6.43 (d, 1H); 6.60 (d, 1H); 7.03 (dd, 1H); 8.44 (d, 1H); 8.90 (s, 2H); 11.34 (s, 1H).

b) 3-(7-amino-4H-quinazolin-3-yl)piperidine-2,6-dione; dihydrochloride

The title compound was obtained in a yield of 81% of theory from the product of Example 7k by adopting the procedure described in Example 9a.

$^1$H-NMR (DMSO-$d_6$): 1.86–1.94 (m, 1H); 2.02–2.33 (m, 2H); 2.40–2.59 (m, 1H); 4.51–4.57 (m, 2H); 5.02–5.08 (m, 1H); 6.68–6.76 (m, 1H); 6.93–7.10 (m, 2H); 8.50–8.56 (m, 1H); 8.96 (s, 2H); 11.27 (s, 1H)

Example 10

3-(7-fluoro-4H-quinazolin-3-yl)1-piperidin-1-ylmethyl-piperidine-2,6-dione 1 ml of aqueous formaldehyde solution (37%) and 0.8 ml of piperidine were added to a suspension of 2.61 g of the product from Example 7e in 50 ml of ethanol. The mixture was stirred for 1 hour at 50° C. and then largely freed from the solvent in vacuo. On adding diethyl ether to the residue 2.83 g (79% of theory) of the title compound were obtained (after separation by filtration and drying in vacuo) in the form of almost colorless crystals.

$^1$H-NMR (DMSO-$d_6$): 1.36–1.48 (m, 6H); 1.95–2.06 (m, 1H); 2.22–2.82 (m, 7H); 4.25 (d, 1H); 4.46 (d, 1H); 4.52–4.68 (m, 3H); 6.66 (dd, 1H); 6.81 (m, 1H); 6.90–6.95 (m, 1H); 7.11 (s, 1H).

Investigation of the Immunomodulating Effectiveness

Stimulation of human monocytes with lipopolysaccharide for the secretion of IL-10 and IL-12:

Human monocytes were isolated from peripheral blood mononuclear cells (PBMC) that had been obtained by means of a ficoll density gradient centrifugation from heparinized full blood. For this purpose the PBMC were incubated with a monoclonal antibody that is directed against the monocyte-specific surface molecule CD14 and on which are coupled superparamagnetic microbeads (Miltenyi Biotech, Bergisch Gladbach). For the positive selection of the marked monocytes from the cell mixture of the PBMC, the total cell suspension was added to a column with ferromagnetic carrier matrix and this was placed in a magnetic field. In this way the cells that were loaded with microbeads were bound to the carrier matrix while unmarked cells passed through the column and were discarded. After removing the matrix from the magnetic field the antibody-loaded cells were eluted by rinsing the now demagnetized column with buffer. The purity of the CD14-positive monocyte population obtained in this way is about 95–98%. These monocytes were incubated for 1 hour at 37° C. and 5% $CO_2$ in a density of $10^6$ cells/ml culture medium (RPMI, supplemented with 10% fetal calf serum) with the test substances dissolved in DMSO. 20 µg/ml LPS from *E. coli* were then added. After 24 hours cell-free culture supernatants were taken and tested for their content of IL-10 as well as IL-12.

The concentration of IL-12 and IL-10 in the cell culture supernatants was determined by means of sandwich ELISAs using two anti-IL-12 and IL-10 monoclonal antibodies (Biosource Europe, Fleurus, Belgium). A reference standard curve with human IL-10 and IL-12 was included. The detection limit of the IL-12 ELISA was 10 pg/ml, and that of the IL-10 ELISA was 15 pg/ml.

TABLE 1

Influence of the test substances compared to thalidomide on the IL-12 and IL-10 production of LPS-activated monocytes

| Example No. | Inhibition of IL-12 Production | | Increase in |
|---|---|---|---|
| | Maximum (%) | IC50 (ng/ml) | IL-10 Production Maximum (%) |
| 1 | 99 | 5 | 360 |
| 3 | 98 | 10 | 230 |
| 7a | 98 | 1 | 365 |
| 7h | 97 | 6 | 316 |
| 7f | 98 | 0.8 | 420 |
| 7n | 84 | 42 | 263 |
| 7m | 89 | 50 | 202 |
| 7i | 96 | 36 | 211 |
| Thalidomide | 80 | 100 | 180 |

The piperidine-2,6-diones heterocyclically substituted in the 3-position of the basic structure described in formula I effectively suppressed the IL-12 production of LPS-activated monocytes in a concentration-dependent manner. Interestingly, the IL-10 production was significantly increased in the same concentration range. The maximum IL-12 inhibition as well as the IC50 values are significantly above those of thalidomide. The most effective compounds are those whose aromatic ring contains a chlorine or fluorine substituent in the 5-position or 7-position or is unsubstituted.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A piperidine-2,6-dione compound heterocyclically substituted in the 3-position and corresponding to formula I,

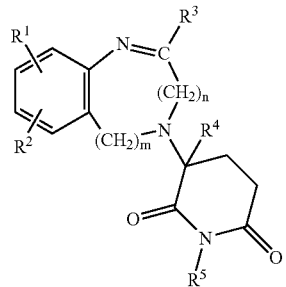

wherein
  $R^1$ and $R^2$, are identical or different and denote H, Br, Cl, F, $CF_3$, OH, $NO_2$, $NH_2$, $N(CH_3)_2$, $C_{1-3}$-alkyl, $C_{1-3}$-alkoxy, phenyl, or together form an annelated benzene ring;
  $R^3$ denotes H, a methyl group or, in the case where a C—N single bond is present, denotes OH, $C_{1-3}$-alkoxy or an [O(CO)$C_{1-3}$-alkyl] group, or together with the C atom forms a carbonyl group;
  $R^4$ denotes H, F, $CF_3$ or $C_{1-3}$-alkyl;
  $R^5$ denotes H, a $CH_2$—OH group or a $CH_2$—$NR^6R^7$ group, in which $R^6$ and $R^7$ are identical or different and denote an alkyl group with 1 to 6 C atoms (straight-chain or branched) or together with the N atom denote a pyrrolidine, piperidine, hexamethyleneimine or morpholine ring;
  n is 0 or 1 and
  m is 0, 1 or 2,
or a salt thereof with a physiologically acceptable acid.

2. The compound of claim 1, wherein said compound is present in the form of a free base.

3. The compound of claim 1, wherein said compound is present in the form of a pure enantiomer.

4. The compound of claim 1, wherein said compound is present in the form of a mixture of stereoisomers.

5. The compound of claim 1, wherein said compound is present in the form of a racemic mixture.

6. The compound of claim 1, wherein $R^1$ and $R^2$ form an annelated benzene ring.

7. The compound of claim 1, wherein $R^1$ and $R^2$, are identical or different and denote H, Br, Cl, F, $CF_3$, $NO_2$, $NH_2$, $C_{1-3}$-alkyl, $C_{1-3}$-alkoxy, or together form an annelated benzene ring, $R^3$ denotes H or OH, $R^4$ denotes H or a methyl group and $R^5$ denotes H or a $CH_2$—$NR^6R^7$group, in which $R^6$ and $R^7$ together with the N atom form a piperidine ring, and n=0 and m=1 or 2.

8. The compound of claim 1, wherein $R^1$ and $R^2$, are identical or different and denote H, Cl, F, $CH^3$ or $NO^2$, $R^3$, $R^4$ and $R^5$ denote hydrogen, n=0 and m=1, and a C=N double bond is present.

9. The compound of claim 8, wherein the groups $R^1$ and $R^2$ are in the 5-position or 7-position.

10. The compound of claim 1, wherein said compound is selected from the group consisting of:
- 3-(7-chloro-4H-quinazolin-3-yl)piperidine-2,6-dione and the corresponding hydrobromide;
- 3-(6-chloro-4H-quinazolin-3-yl)piperidine-2,6-dione and the corresponding hydrobromide;
- 3-(4H-quinazolin-3-yl)piperidine-2,6-dione and the corresponding hydrobromide or hydrochloride;
- 3-(2-hydroxy-1,4-dihydro-2H-quinazolin-3-yl)piperidine-2,6-dione;
- 3-(6-methoxy-4H-quinazolin-3-yl)piperidine-2,6-dione and the corresponding hydrochloride;
- 3-(5-chloro-4H-quinazolin-3-yl)piperidine-2,6-dione;
- 3-(8-chloro-4H-quinazolin-3-yl)piperidine-2,6-dione;
- 3-(6-fluoro-4H-quinazolin-3-yl)piperidine-2,6-dione;
- 3-(8-methoxy-4H-quinazolin-3-yl)piperidine-2,6-dione and the corresponding hydrochloride;
- 3-(7-fluoro-4H-quinazolin-3-yl)piperidine-2,6-dione and the corresponding hydrochloride;
- 3-(4H-benzo[g]quinazolin-3-yl)piperidine-2,6-dione;
- 3-(5-fluoro-4H-quinazolin-3-yl)piperidine-2,6-dione;
- 3-(5-nitro-4H-quinazolin-3-yl)piperidine-2,6-dione;
- 3-(7-trifluoromethyl)-4H-quinazolin-3-yl)piperidine-2,6-dione;
- 3-(7-nitro-4H-quinazolin-3-yl)piperidine-2,6-dione;
- 3-(8-bromo-6-methyl-4H-quinazolin-3-yl)piperidine-2,6-dione;
- 3-(5-methyl-4H-quinazolin-3-yl)piperidine-2,6-dione;
- 3-(6,7-difluoro-4H-quinazolin-3-y])piperidine-2,6-dione;
- 3-methyl-3-(4H-quinazolin-3-yl)piperidine-2,6-dione;
- 3-(4,5-dihydrobenzo[d][1,3]diazepin-3-yl)piperidine-2,6-dione;
- 3-(5-amino-4H-quinazolin-3-yl)piperidine-2,6-dione and the corresponding dihydrochloride;
- 3-(7-amino-4H-quinazolin-3-yl)piperidine-2,6-dione and the corresponding dihydrochloride and
- 3-(7-fluoro-4H-quinazolin-3-yl)1-piperidine-1-ylmethyl-piperidine-2,6-dione.

11. A process for producing a piperidine-2,6-dione corresponding to formula I according to claim 1, comprising the steps of:
alkylating an amino compound corresponding to formula II

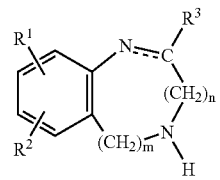

with a 3-bromopiperidine-2,6-dione compound corresponding to formula III

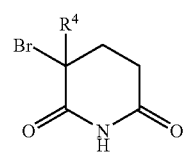

to form a compound corresponding to formula IA,

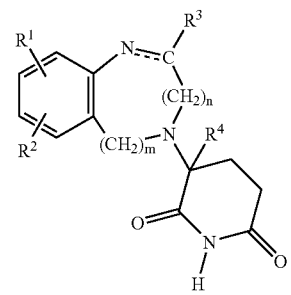

wherein in the compound corresponding to formula I if $R^5$ does not denote hydrogen this group is introduced by reaction with formaldehyde optionally together with an amimne of the general formula $HNR^6R^7$, wherein $R^6$ and $R^7$ are as defined in claim 1, and if $R^4$ denotes hydrogen, then in order to produce further compounds where $R^4=F$, $CF^3$ or $C_{1-3}$-alkyl, $R^4$ is replaced by alkylation or halogenation.

12. The process of claim 11, wherein $R^5$ does not denote hydrogen and is introduced by reaction with formaldehyde together with an amine corresponding to formula $HNR^6R^7$.

13. A process for producing a piperidine-2,6-dione according to claim 1, comprising the steps of alkylating an an amino compound corresponding to formula II

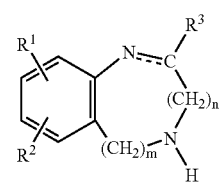

with a 3-bromopiperidine-2-one compound corresponding to formula IV

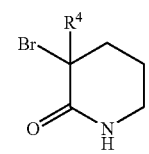

to form a compound corresponding to formula IB and

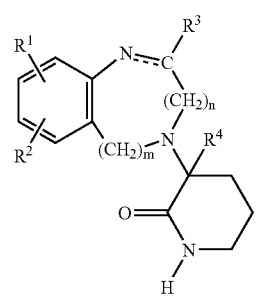

oxidizing said compound corresponding to formula IB to form a compound corresponding to formula IA

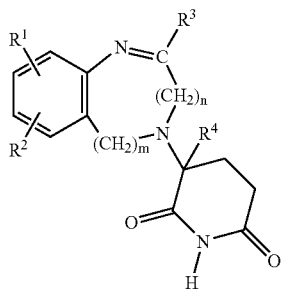

14. The process of claim 13, wherein said oxidizing step is carried out with m-chloroperbenzoic acid or ruthenium (IV) oxide and sodium periodate.

15. The process of claim 13, wherein in the compound corresponding to formula I if $R^5$ does not denote hydrogen this group is introduced by reaction with formaldehyde optionally together with an amine of the general formula $HNR^6R^7$, wherein $R^6$ and $R^7$ are defined as in claim 1, and if the group $R^4$ denotes hydrogen, then in order to produce further compounds where $R^4$=F, $CF^3$ or $C_{1-3}$-alkyl, $R^4$ is replaced by alkylation or halogenation.

16. The process of claim 15, wherein $R^5$ does not denote hydrogen and is introduced by reaction with formaldehyde together with an amine corresponding to formula $HNR^6R^7$.

17. A process for producing a piperidine-2,6-dione compound according to claim 1, wherein m=1 and n=0 and $R^3$ denotes H or OH, comprising the steps of:

oxidizing a formamide compound corresponding to formula VI,

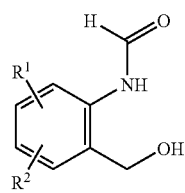

which is accessible by selective N-formylation of the corresponding 2-aminobenzyl alcohol or by selective O-deformylation of the N,O-bisformyl compound, to form a benzaldehyde corresponding to formula VII

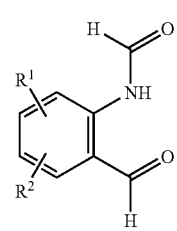

converting said benzaldehyde corresponding to formula VII by reductive amination with glutamine using complex boron hydrides into a compound corresponding to formula VIII,

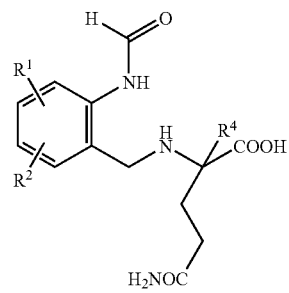

cyclizing said compound corresponding to formula VIII in the presence of at least one activating reagent, to form a glutarimide corresponding to formula IX, and

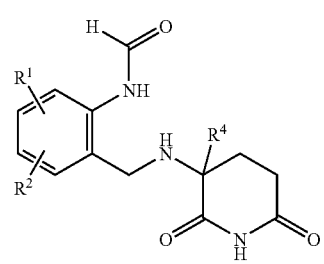

in step A, converting the compound corresponding to formula IX in protic solvents under acid catalysis to form a compound corresponding to formula I in which m is 1, n is 0, a C=N double bond is present, and $R^3$ or $R^5$ denote hydrogen, or in step B, converting the compound corresponding to formula IX, in which the amine function is protected by a protective group, by hydrogenolytic splitting off of this protective group to form a compound corresponding to formula I in which a C—N single bond is present and $R^3$ denotes a hydroxy group.

18. The process of claim 17, wherein the step of cyclizing said compound corresponding to formula VIII is performed in the presence of N,N'-carbonyl diimidazole.

19. The process of claim 17, wherein before said glutarimide corresponding to formula IX is formed, the amine function of said compound corresponding to formula VIII is protected by a protective group, which is then split off again.

20. The process of claim 19, wherin said protective group is a benzyloxycarbonyl group.

21. The process of claim 17, wherein in the compound corresponding to formula I in step A, if $R^5$ does not denote hydrogen then this group is introduced by reaction with formaldehyde optionally together with an amine of the general formula $HNR^6R^7$, wherein $R^6$ and $R^7$ are defined in claim 1, and if $R^4$ denotes hydrogen, then in order to produce further compounds where $R^4$=F, $CF^3$ or $C_{1-3}$-alkyl, $R^4$ is replaced by alkylation or halogenation.

22. The process of claim 21, wherein $R^5$ does not denote hydrogen and is introduced by reaction with formaldehyde together with an amine corresponding to formula $HNR^6R^7$.

23. The process of claim 17, wherein in step B, said compound corresponding to formula IX is converted, with dilute acids in organic solvents by splitting off water, into compounds corresponding to formula I with a C=N double bond and where $R^3$=hydrogen.

24. A process for producing a piperidine-2,6-dione compound according to claim 1, in which m=1 and n=0 and $R^3$ denotes H, comprising the steps of:

preparing a compound corresponding to formula VII

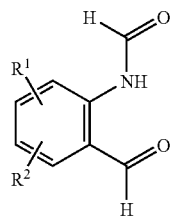

VII reductively aminating said compound;
treating the reaction mixture with acids;
converting said compound into a compound corresponding to formula X

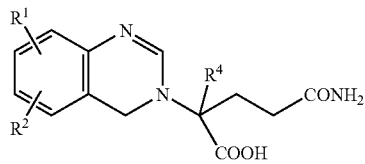

X converting said compound corresponding to formula X by cyclization into a compound corresponding to formula I with a C=N double bond.

25. The process of claim 24, wherein in the compound corresponding to formula I, if $R^5$ does not denote hydrogen this group is introduced by reaction with formaldehyde optionally together wiht an amine of the general fomrula $HNR^6R^7$, wheren $R^6$ and $R^7$ are as defined in claim 1, and if $R^4$ denotes hydrogen, then in order to produce further compounds where $R^4$=F, $CF^3$ or $C_{1-3}$-alkyl, $R^4$ is replaced by alkylation or halogenation.

26. The process of claim 25, wherein $R^5$ does not denote hydrogen and is introduced by reaction with formaldehyde together with an amine corresponding to formula $HNR^6R^7$.

27. A process according to claim 24, wherein compounds corresponding to formula I but where m=2 are prepared.

28. A pharmaceutical formulation, comprising:
a compound corresponding to formula I of claim 1 and an auxiliary agent.

29. The pharmaceutical composition of claim 28, wherein said compound is present in the form of a free base.

30. The pharmaceutical composition of claim 28, wherein said compound is present in the form of a salt with a base.

31. The pharmaceutical composition of claim 28, wherein said compound is present in the form of a pure enantiomer.

32. The pharmaceutical composition of claim 28, wherein said compound is present in the form of mixture of stereoisomer.

33. The pharmaceutical composition of claim 28, wherein said compound is present in the form of a racemic mixture.

* * * * *